United States Patent [19]

Janssen et al.

[11] Patent Number: 4,652,580
[45] Date of Patent: Mar. 24, 1987

[54] APPLICATION OF AZOLYLMETHYLOXIRANES FOR THE TREATMENT OF VIRAL DISEASES

[75] Inventors: Bernd Janssen; Stefan Karbach, both of Ludwigshafen; Norbert Meyer, Ladenburg; Gerhard Laur, Mannheim, all of Fed. Rep. of Germany

[73] Assignee: BASF Aktiengesellschaft, Fed. Rep. of Germany

[21] Appl. No.: 839,948

[22] Filed: Mar. 17, 1986

[30] Foreign Application Priority Data

Mar. 29, 1985 [DE] Fed. Rep. of Germany ....... 3511411

[51] Int. Cl.⁴ .................... A61K 31/41; A61K 31/415
[52] U.S. Cl. .................................... 514/383; 514/397
[58] Field of Search ................................ 514/383, 397

[56] References Cited

U.S. PATENT DOCUMENTS 4,564,622 1/1986 Streissle et al. ..................... 514/383

FOREIGN PATENT DOCUMENTS 3238903 4/1984 Fed. Rep. of Germany .

3315808 10/1984 Fed. Rep. of Germany .......... 249/8

OTHER PUBLICATIONS

Chemical Abstracts 100:85704p (1984).
Chemical Abstracts 100:103357j (1984).
Burger's Medicinal Chemistry, IV edition, 1979, part 2, pp. 554 et seq.

Primary Examiner—Jerome D. Goldberg
Attorney, Agent, or Firm—Keil & Weinkauf

[57] ABSTRACT

The application of compounds of the formula

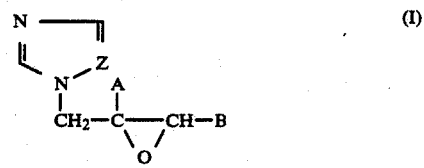

where A, B and Z have the meanings stated in the description, for the treatment of viral infections is described.

2 Claims, No Drawings

APPLICATION OF AZOLYLMETHYLOXIRANES FOR THE TREATMENT OF VIRAL DISEASES

It is known that azole derivatives, eg. 2-α-hydroxybenzyl)-benzimidazole (cf. Burger's Medicinal Chemistry, IV. edition, 1979, part 2, page 554 et seq.) and hydroxyethylazoles, eg. 2-(4-chlorophenoxymethyl)-3,3-dimethyl-1-(1,2,4-triazol-1-yl)-2-butanol (=vibunazole, German Laid-Open Application DOS No. 3,238,903), as well as other members of this class of substances (German Laid-Open Application DOS No. 3,315,808), display antiviral activity. Azolylmethyloxiranes of the formula I

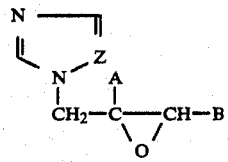

where A and B are identical or different and are each alkyl of 1 to 4 carbon atoms, naphthyl, biphenyl or phenyl, and phenyl may be substituted by halogen, nitro, alkyl, alkoxy or haloalkyl, each of 1 to 4 carbon atoms, phenoxy or phenylsulfonyl, and Z is a CH group of a nitrogen atom, and their physiologically tolerated addition salts with acids are known to be highly effective local and systemic antimycotics (German Laid-Open Application DOS No. 3,218,129).

Surprisingly, we have found that the above azolylmethyloxiranes of the formula I also possess a very good antiviral action.

The compounds of the formula I contain chiral centers and are obtained in general in the form of racemates or diastereomer mixtures of erythro and threo forms. The erythro and threodiastereomers of the novel compounds can be separated, for example, on the basis of their different solubilities or by column chromatography, and can be isolated in pure form. Pure enantiomers can be obtained from such pure diasteromer pairs by conventional methods. Both the pure diastereomers or enantiomers and the mixtures of these obtained in the synthesis can be used as antiviral active compounds.

Specific examples of compounds of the formula I are the following:

| No. | A | B | Z | Diastereomer | Mp. [°C.] |
|---|---|---|---|---|---|
| 1 | 4-Cl—$C_6H_4$ | 2,4-$Cl_2$—$C_6H_3$ | CH | A | 102–103 |
| 2 | 4-Cl—$C_6H_4$ | 2,4-$Cl_2$—$C_6H_3$ | CH | B | 109 |
| 3 | 4-Cl—$C_6H_4$ | 2,4-$Cl_2$—$C_6H_3$ | N | A | 119 |
| 4 | 4-Br—$C_6H_4$ | $C_6H_5$ | CH | A | 152–153 |
| 5 | 4-Br—$C_6H_4$ | 4-Cl—$C_6H_4$ | CH | A | 143–144 |
| 6 | $C_6H_5$ | 2,4-$Cl_2$—$C_6H_3$ | CH | A | 103 |
| 7 | 4-Br—$C_6H_4$ | 2,4-$Cl_2$—$C_6H_3$ | CH | A | 107–100 |
| 8 | 4-4-$Cl_2$—$C_6H_3$ | 4-Cl—$C_6H_4$ | CH | A | 135 |
| 9 | 4-Cl—$C_6H_4$ | $C_6H_5$ | CH | A | 138 |
| 10 | 4-Br—$C_6H_4$ | 2,4-$Cl_2$—$C_6H_3$ | N | A | 133–134 |
| 11 | $CH_3$ | 2,4-$Cl_2$—$C_6H_3$ | CH | B | 113–117.5 |
| 12 | $CH_3$ | 2,4-$Cl_2$—$C_6H_3$ | CH | A | 98–104 |
| 13 | $C(CH_3)_3$ | 4-Cl—$C_6H_4$ | N | A | 79–80 |
| 14 | $C(CH_3)_3$ | 4-Cl—$C_6H_4$ | CH | A.×HCl | 214–216 |
| 15 | $C(CH_3)_3$ | $C_6H_5$ | N | A ×HCl | 148 |
| 16 | $C(CH_3)_3$ | $C_6H_5$ | CH | A | 75 |
| 17 | $C(CH_3)_3$ | 2,4-$Cl_2$—$C_6H_3$ | N | A | 124 |
| 18 | $C(CH_3)_3$ | 2,4-$Cl_2$—$C_6H_3$ | CH | A | 95 |
| 19 | 4-Cl—$C_6H_4$ | 4-$C(CH_3)_3$—$C_6H_4$ | CH | B | 160–162 |
| 20 | 4-Cl—$C_6H_4$ | 4-$C(CH_3)_3$—$C_6H_4$ | N | A | 176–177 |
| 21 | 2,4-$Cl_2$—$C_6H_3$ | 4-$C(CH_3)_3$—$C_6H_4$ | CH | A | 132–134 |
| 22 | $CH_3$ | 2,4-$Cl_2$—$C_6H_3$ | N | A | 105–108 |
| 23 | $CH_3$ | 2,4-$Cl_2$—$C_6H_3$ | N | B | 80–85 |
| 24 | $CH_3$ | 2,4-$Cl_2$—$C_6H_3$ | N | A:B = 1:1 | 70–81 |
| 25 | 4-$C(CH_3)_3$—$C_6H_4$ | 4-Cl—$C_6H_4$ | CH | A | 100–152 |
| 26 | 4-$C(CH_3)_3$—$C_6H_4$ | 4-Cl—$C_6H_4$ | N | A | 105–107 |
| 27 | 4-$C(CH_3)_3$—$C_6H_4$ | 2,4-$Cl_2$—$C_6H_3$ | CH | A | 101–113 |
| 28 | 4-$C(CH_3)_3$—$C_6H_4$ | 2,4-$Cl_2$—$C_6H_3$ | N | A | 100–111 |
| 29 | 4-Cl—$C_6H_4$ | 3-$OCH_3$—$C_6H_4$ | CH | A ×H Cl | 173 |
| 30 | 4-Cl—$C_6H_4$ | 3-$OCH_3$—$C_6H_4$ | N | A | 77 |
| 31 | $C_6H_5$ | 2,4-$Cl_2$—$C_6H_3$ | N | A | 159–161 |
| 32 | 4-Cl—$C_6H_4$ | 3-$Cf_3$—$C_6H_4$ | CH | A | 101–104 |
| 33 | 4-Cl—$C_6H_4$ | 3-$CF_3$—$C_6H_4$ | N | A | 107–109 |
| 34 | $C_6H_5$ | 3-$CF_3$—$C_6H_4$ | CH | A | 77–78.5 |
| 35 | $C_6H_5$ | 3-$CF_3$—$C_6H_4$ | N | A ×H Cl | 131–133 |
| 36 | $C_6H_5$ | $C_6H_5$ | CH | A | 108–110 |
| 37 | 4-Cl—$C_6H_4$ | 4-F—$C_6H_4$ | CH | A | 130–132 |
| 38 | $C_6H_5$ | 4-Cl—$C_6H_4$ | CH | A | 105–106 |
| 39 | $C_6H_5$ | $C_6H_5$ | N | A | 116–118 |
| 40 | $C_6H_5$ | 4-Cl—$C_6H_4$ | N | A | 114–115 |
| 41 | 4-Cl—$C_6H_4$ | $C_6H_5$ | N | A | 106–110 |
| 42 | 4-$C_6H_5$—$C_6H_4$ | 4-Cl—$C_6H_4$ | N | A | 163–165 |
| 43 | 4-Br—$C_6H_4$ | $C_6H_5$ | N | A | 115–120 |
| 44 | 4-Br—$C_6H_4$ | 4-Cl—$C_6H_4$ | N | A | 115–120 |
| 45 | 4-Cl—$C_6H_4$ | 4-L—$C_6H_4$ | N | A | 112–117 |
| 46 | 4-Cl—$C_6H_4$ | 4-Br—$C_6H_4$ | N | A | 115–119 |
| 47 | 4-Cl—$C_6H_4$ | 4-Br—$C_6H_4$ | CH | A | 114–116 |
| 48 | 4-Cl—$C_6H_4$ | 4-Br—$C_6H_4$ | CH | B | 179–181 |
| 49 | 2,4-$Cl_2$—$C_6H_3$ | 4-Br—$C_6H_4$ | CH | A | 135–139 |
| 50 | 4-Cl—$C_6H_4$ | 4-F—$C_6H_4$ | N | B | 219–223 |

-continued

| No. | A | B | Z | Diastereomer | Mp. [°C.] |
|---|---|---|---|---|---|
| 51 | 4-Cl—$C_6H_4$ | 4-Br—$C_6H_4$ | N | B | 210–211 |
| 52 | 2,4-$Cl_2$—$C_6H_3$ | 4-Br—$C_6H_4$ | N | A | 108–110 |
| 53 | 2,4-$Cl_2$—$C_6H_3$ | $C_6H_5$ | CH | A | Resin |
| 54 | 2,4-$Cl_2$—$C_6H_3$ | $C_6H_5$ | CH | B | 118–121 |
| 55 | 2,4-$Cl_2$—$C_6H_3$ | $C_6H_5$ | N | A | Resin |
| 56 | 2,4-$Cl_2$—$C_6H_3$ | $C_6H_5$ | N | B | Resin |
| 57 | 4-($SO_2$—$C_6H_5$)—$C_6H_4$ | 4-Cl—$C_6H_4$ | CH | A | 193–195 |
| 58 | 4-($SO_2$—$C_6H_5$)—$C_6H_4$ | 4-Cl—$C_6H_4$ | CH | B | 204–205 |
| 59 | 4-($SO_2$—$C_6H_5$)—$C_6H_4$ | 4-Cl—$C_6H_4$ | N | A | 132–135 |
| 60 | 4-($SO_2$—$C_6H_5$)—$C_6H_4$ | 4-Cl—$C_6H_4$ | N | B | 175–177 |
| 61 | 2,4-$Cl_2$—$C_6H_3$ | 4-Cl—$C_6H_4$ | N | A | |
| 62 | 4-$C_6H_5$—$C_6H_4$ | 4-Cl—$C_6H_4$ | CH | | |
| 63 | 2-Cl—$C_6H_4$ | 4-Cl—$C_6H_4$ | CH | | |
| 64 | 2-Cl—$C_6H_4$ | 4-Cl—$C_6H_4$ | N | | |
| 65 | 4-Cl—$C_6H_4$ | 3-Cl—$C_6H_4$ | CH | | |
| 66 | 4-Cl—$C_6H_4$ | 3-Cl—$C_6H_4$ | N | | |
| 67 | $C_6H_5$ | 3,4-$Cl_2$—$C_6H_3$ | CH | B | 103–105 |
| 68 | $C_6H_5$ | 3,4-$Cl_2$—$C_6H_3$ | N | A | Resin |
| 69 | 3,5-$Cl_2$—$C_6H_3$ | 4-Cl—$C_6H_4$ | CH | | |
| 70 | 3,5-$Cl_2$—$C_6H_3$ | 4-Cl—$C_6H_4$ | N | | |
| 71 | 2-$OCH_3$—$C_6H_4$ | 2,4-$Cl_2$—$C_6H_3$ | CH | | |
| 72 | 2-$OCH_3$—$C_6H_4$ | 2,4-$Cl_2$—$C_6H_3$ | N | | |
| 73 | 4-O—$C(CH_3)_3$—$C_6H_4$ | 2,4-$Cl_2$—$C_6H_3$ | CH | | |
| 74 | 4-O—$C(CH_3)_3$—$C_6H_4$ | 2,4-$Cl_2$—$C_6H_3$ | N | | |
| 75 | 4-$CH_3$—$C_6H_4$ | $C_6H_5$ | CH | | |
| 76 | 4-$CH_3$—$C_6H_4$ | $C_6H_5$ | N | | |
| 77 | 4-(O—$C_6H_5$)—$C_6H_4$ | 4-Br—$C_6H_4$ | CH | | |
| 78 | 4-(O—$C_6H_5$)—$C_6H_4$ | 4-Br—$C_6H_4$ | | | |
| 79 | $C_6H_5$ | 4-$NO_2$—$C_6H_4$ | CH | | |
| 80 | $C_6H_5$ | 4-$NO_2$—$C_6H_4$ | N | | |
| 81 | 2-$C_{10}H_7$ | 2,4-$Cl_2$—$C_6H_3$ | CH | A | 135 |
| 82 | 2-$C_{10}H_7$ | 2,4-$Cl_2$—$C_6H_3$ | N | A | 151 |
| 83 | 4-Cl—$C_6H_4$ | 1-$C_{10}H_7$ | CH | | |
| 84 | 4-Cl—$C_6H_4$ | 1-$C_{10}H_7$ | N | | |
| 85 | 4-Cl—$C_6H_4$ | 4-Cl—$C_6H_4$ | CH | A | 115–120 |
| 86 | 4-Cl—$C_6H_4$ | 4-Cl—$C_6H_4$ | N | A | 105–108 |
| 87 | 2-$C_{10}H_7$ | 4-Cl—$C_6H_4$ | CH | A | 140 |
| 88 | 2-$C_{10}H_7$ | 4-Cl—$C_6H_4$ | N | A | 107 |
| 89 | 2,4-$Cl_2$—$C_6H_3$ | 4-$C(CH_3)_3$—$C_6H_4$ | CH | B | 142–143 |
| 90 | 3,4-$Cl_2$—$C_6H_3$ | 4-Br—$C_6H_4$ | N | A | 130–134 |
| 91 | 4-Br—$C_6H_4$ | 4-F—$C_6H_4$ | N | A | 137 |
| 92 | 4-Br—$C_6H_4$ | 4-F—$C_6H_4$ | N | B | Oil |
| 93 | 4-Br—$C_6H_4$ | 4-F—$C_6H_4$ | CH | A | 152 |
| 94 | $C_6H_5$ | 2-Cl—$C_6H_4$ | N | A | 158–159 |
| 95 | 4-Cl—$C_6H_4$ | 2-Cl—$C_6H_4$ | N | A | 166 |
| 96 | $C_6H_5$ | 2-Cl—$C_6H_4$ | CH | A/B = 65:35 | 85–87 |
| 97 | 4-Cl—$C_6H_4$ | 2-Cl—$C_6H_4$ | CH | A/B = 70:30 | 90–92 |

Preferred compounds of the formula I are those in which A and B are each 3-chlorophenyl, 4-bromophenyl, 3-trifluoromethylphenyl, 2,6-dichlorophenyl, 4-tert-butylphenyl or in particular phenyl, 2-chlorophenyl, 4-chlorophenyl or 2,4-dichlorophenyl.

Antiviral agents can be prepared using either the pure diastereomers of enantiomers or their mixtures.

Conventional acids preferably used for the formation of physiologically tolerated salts are hydrohalic acids, eg. hydrochloric acid and hydrobromic acid, in particular hydrochloric acid, with which the novel compounds form particularly readily crystallizing salts, as well as phosphoric acid, nitric acid, sulfuric acid, monofunctional and bifunctional carboxylic acids and hydroxycarboxylic acids, such as acetic acid, oxalic acid, maleic acid, succinic acid, fumaric acid, tartaric acid, citric acid, salicylic acid, sorbic acid or lactic acid, and sulfonic acids, such as p-toluenesulfonic acid and naphthalene-1,5-disulfonic acid.

The compounds can be prepared by methods similar to those described in German Laid-Open Applications DOS Nos. 3,218,129 and 3,218,130.

For example, a compound of the formula II

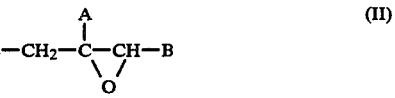

where A and B have the stated meanings and L is a leaving group which can be displaced by nucleophilic substitution, can be reacted with a compound of the formula III

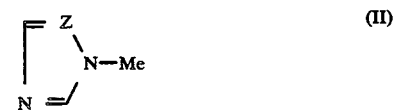

where Me is hydrogen or a metal atom and Z is a CH group or nitrogen.

Where Me is hydrogen, the reaction is carried out in the presence or absence of a solvent or diluent, with or without the addition of an inorganic base and with or without the addition of a reaction accelerator, at from 10° to 120° C. The preferred solvents or diluents include ketones, such as acetone, methyl ethyl ketone or cyclohexanone, nitriles, such as acetonitrile, esters, such as ethyl acetate, ethers, such as diethyl ether, tetrahydrofuran or dioxane, sulfoxides, such as dimethylsulfoxide, amides such as dimethylformamide, dimethylacetamide or N-methylpyrrolidone, and sulfolane, as well as mixtures of these.

Examples of suitable bases, which may also be used as acid acceptors in the reaction, are alkali metal hydroxides, such as lithium hydroxide, sodium hydroxide or potassium hydroxide, alkali metal carbonates, such as sodium carbonate, potassium carbonate, sodium bicarbonate or potassium bicarbonate, an excess of 1,2,4-triazole, pyridine or 4-dimethylaminopyridine. Other conventional bases may also be used.

Preferred reaction accelerators are metal halides, such as sodium iodide, potassium iodide, quaternary ammonium salts, such as tetrabutylammonium chloride, bromide or iodide or benzyltriethylammonium chloride or bromide, and crown ethers, such as 12-crown-4, 15-crown-5, 18-crown-6, dibenzo-18-crown-6 or dicyclohexano-18-crown-6.

The reaction is carried out in general at from 20° to 150° C. under atmospheric or superatmospheric pressure, continuously or batchwise.

Where Me is a metal atom, the reaction is carried out in the presence or absence of a solvent or diluent and with or without the addition of a strong inorganic or organic base, at from −10° to 120° C. The preferred solvents or diluents include amides, such as dimethylformamide, diethylformamide, dimethylacetamide, diethylacetamide, N-methylpyrrolidone, hexamethylphosphorotriamide, sulfoxides, such as dimethyl sulfoxide and finally sulfolane.

Examples of suitable bases, which may also be used as acid acceptors in the reaction, are alkali metal hydrides, such as lithium hydride, sodium hydride or potassium hydride, alkali metal amides, such as sodium amide or potassium amide, and sodium tert-butoxide, potassium tert-butoxide, triphenylmethyl-lithium, -sodium and -potassium and naphthalene-lithium, -sodium and -potassium.

The resulting compounds of the formula I are isolated by a conventional method, if necessary purified and, if desired, converted to their salts with physiologically tolerated acids.

The compounds of the formula I possess powerful antiviral activity, especially against herpes viruses, as shown in the Examples below (vibunazole is used as a comparative compound).

EXAMPLE A

Cell culture experiments

Herpes Simplex Virus (HSV) and human cytomegalovirus multiply readily in cultures of monkey kidney cells. The infections are distinguished by characteristic cytopathic effects (CPE) which occur about 8–12 hours after infection and can easily be observed and assessed. Antiviral properties of test substances which are non-toxic for the host cells or display their action against the infecting viruses in a concentration which is non-toxic for the cells can be readily characterized by the reduction of the cytopathic effect in this system.

The cells used were monkey kidney cells of the strain RC-37 Rita (Italodiagnostics, Rome), which were cultured in basal Eagle's medium (BME; Eagle, H., J. Exp. Med. 102, (1955), 595–601) until infection with the HSV-1 strains ANG (Schröder et al., Intervirology 6, (1976), 270–284) and WAL (Kirchner et al., J. Immunol. 117, (1978), 1753). On infection with the virus, the BME medium was replaced with medium 199 (Morgan et al., Proc. Soc. Exp. Biol., Med. 73 (1950), 1–8). The cells were infected after the formation of an almost confluent lawn with a multiplicity of two infectious virus particles [=2 PFU (plaque forming units)] per cell. The suspensions of the virus strains had titers of from $2 \times 10^7$ to $1 \times 10^8$ PFU/ml. The test substances were introduced in non-cytotoxic concentration into the medium of the infected cells at various times from 1 hour before to 2 hours after infection. The cytotoxicity limits were tested on the basis of growth curves and the colony-forming ability of isolated cells. The action of the substances was monitored in comparison with control cultures both by microscopic observation and by determining the progeny cell viruses. The virus titer was determined as described by Russell (Nature, London, 195 (1962), 1028–1029).

The compounds of the present invention exhibited substantially better inhibition of the CPE than vibunazole. The virus titer determined after application of the compounds I, in particular substance No. 3, was also substantially lower than in the case of the comparative compound.

EXAMPLE B

Testing the antiviral activity in the mouse model of the HSV infection

The experimental HSV infection of susceptible inbred strains of mice is today a well established, widely used experimental system for studying the pathogenicity of herpes viruses (Zisman et al., J. Immunol. 104 (1970), 1155–1159; Stevens and Cook, J. Epth. Med. 133 (1971), 19–38; Lopez, Nature London, 258 (1975), 152–153; Kirchner et al., Zeitsch. f. Immunitätsforsch. und exp. Therapie, 154 (1978), 147–154 and Kaerner et al., J. Virol., 46 (1983), 83–93). After peripheral (intraperitoneal) infection of mice with HSV-1, the infection initially spreads in the spleen; subsequently (from 3 to 4 days after infection), the virus attacks the central nervous system of the animals, passes into the brain and kills the mice about 8–10 days after infection by causing encephalitis. Compared with other peripheral methods of infection (eg. intravaginal, etc.), intraperitoneal infection has the advantage that metering can be carried out more exactly.

In the present tests, mice were infected intraperitoneally with with $10^6$ PFU of HSV-1 WAL per animal. The substances to be tested were likewise administered intraperitoneally to the infected animals at various times after infection. The course of the disease was recorded. For all mice (both those which were killed and those which survived), the brains were examined for the presence of the infectious virus.

Administration of the compounds of the present invention, for example compound 3, resulted in a significant reduction in the mortality rate compared with the controls. The comparative compound had no effect in this respect.

EXAMPLE C

Testing the antiviral action in the guinea-pig (cutaneous infection model)

These tests were carried out essentially in accordance with the instructions given by Huber et al. (J. Invest. Dermatol. 62 (1974), 92–95).

Guinea-pigs weighing 400-500 g were epilated in the region of the rear flank, anesthetized with nembutal and infected intracutaneously with HSV-1 WAL (about $1\times10^5$ to $5\times10^5$ PFU/animal) using a Buntscheid multiple-needle gun. The substances to be tested were administered perorally by gavage at various times, (from 2 to 48 hours) after infection. The development and healing of virally caused lesions at the points of infection were monitored, and documented photographically.

While administration of the comparative compound had a statistically insignificant effect on the course of the infection compared with untreated controls, the compounds of the present invention, eg. compound 3, resulted in less pronounced development and more rapid healing of these virally caused lesions when used in the same dose.

The compounds of the formula I are therefore particularly useful for the enteral, parenteral and external treatment of DNA virus infections in humans and animals and thus constitutes a valuable enrichment of therapy. The following indications are specific examples of the application in humans: herpes labialis, herpes genitalis, herpes Zoster (shingles), varicella (chickenpox), keratoconjunctivitis herpetica, infectious mononucleosis and cytomegalovirus infections. Particular areas of use in veterinary medicine are pseudorabies virus infections in pigs and cattle, rhinotracheritis virus infections in cattle, rhinopneumonitis virus infections in horses and Marek's disease in hens.

The compounds can be used alone or together with other known active compounds, in particular antibiotics.

The chemotherapeutic agents or formulations are prepared in a conventional manner, in particular by mixing an appropriate dose with the conventional solid, semi-solid or liquid carriers or diluents and the conventional pharmaceutical auxiliaries, in accordance with the desired route of administration (cf. H. Sucker et al., Pharmazeutische Technologie, Thieme-Verlag, Stuttgart, 1978).

Examples of suitable forms for administration are tablets, coated tablets, capsules, pills, suppositories, aqueous solutions, suspensions and emulsions, and where appropriate sterile injectable solutions, non-aqueous emulsions, suspension and solutions, ointments, creams, pastes, lotions, etc.

The therapeutically active compound is preferably present in the pharmaceutical formulations in a concentration of from 0.5 to 90% by weight, based on the total mixture.

To achieve the desired results in the case of oral administration either in human or in veterinary medicine, the active compound or compounds can be administered in general in amounts of from about 0.1 to about 10.0, preferably from 0.2 to 6, mg/kg of body weight per day, preferably in the form of several single doses. However, is may be necessary to deviate from the stated doses, and to do this as a function of the nature and severity of the disorder, the type of formulation and the route of administration of the drug, as well as the period or interval between administrations. Thus, it may be sufficient in some cases to use less than the abovementioned amount of active compounds, while in other cases the above amount of active compound has to be exceeded.

Examples of pharmaceutical formulations:

EXAMPLE I

Tablets containing 250 mg of active compound Composition for 1000 tablets:

| | |
|---|---|
| Active compound No. 3 | 250 g |
| Potato starch | 100 g |
| Lactose | 50 g |
| Gelatine solution (4% strength) | 45 g |
| Talc | 10 g |

Preparation:

The finely powdered active compound, potato starch and lactose are mixed, the mixture is moistened thoroughly with the gelatine solution and then granulated to give fine particles, and the granules are dried. The dry granules are sieved and then mixed with talc, and the mixture is pressed in a rotary tableting machine to give tablets. The tablets are introduced into polypropylene containers which are closed tightly.

EXAMPLE II

Cream containing 1% of active compound

| | |
|---|---|
| Active compound No. 3 | 1.0 g |
| Glycerol monostearate | 10.0 g |
| Cetyl alcohol | 4.0 g |
| Polyethylene glycol-400 stearate | 10.0 g |
| Polyethylene glycol sorbitan monostearate | 10.0 g |
| Propylene glycol | 6.0 g |
| Methyl p-hydroxybenzoate | 0.2 g |
| Deionized water, to make up to | 100.0 g |

Preparation:

The very finely powdered active compound is suspended in propylene glycol, and the suspension is stirred into a melt, at 65° C., comprising glycerol monostearate, cetyl alcohol, polyethylene glycol-400 stearate and polyethylene glycol sorbitan monostearate. A solution, at 70° C., of methyl p-hydroxybenzoate in water is emulsified in this mixture, the emulsion is cooled, and the resulting cream is homogenized in a colloid mill and then introduced into tubes.

EXAMPLE III

Powder containing 1% of active compound

| | |
|---|---|
| Active compound No. 3 | 1.0 g |
| Zinc oxide | 10.0 g |
| Magnesium oxide | 10.0 g |
| Finely divided silica | 2.5 g |
| Magnesium stearate | 1.0 g |
| Talc | 75.5 g |

Preparation:

The active compound is micronized in a jet mill employing air, and is then mixed with the other components to give a homogeneous mixture. This is forced through a sieve of No. 7 mesh size and then introduced into polyethylene containers with a dusting attachment.

The Examples which follow illustrate the preparation of the compounds of the formula I. Preparation of the starting materials

Example a 63.6 g of potassium tert-butylate in 300 ml of dry methanol were introduced into a solution of 229 g of 2,4-dichlorobenzyltriphenylphosphonium chloride in 800 ml of dry methanol at 10° C., and 77.2 g of 4-chloroacetophenone were added after 0.5 hour. The reaction solution was refluxed for 3 hours, after which the precipitated salt was filtered off at room temperature and the filtrate was evaporated down under reduced pressure. By dispersing the residue with petroleum ether (50°-70° C.), triphenylphosphine oxide was separated off, and the solution was evaporated down under reduced pressure. The residue was taken up in 1 l of carbon tetrachloride, and the solution was refluxed with 81.7 g of N-bromosuccinimide and 4 g of 2,2'-azobisisobutyronitrile. When the reaction was completed, the succinimide was filtered off, the filtrate was evaporated down under reduced pressure and the residue was recrystallized from methanol. 73.4 g (38.8%) of Z-1-(2,4-dichlorophenyl)-2-(4-chlorophenyl)-3-bromo-prop-1-ene of melting point 128° C. were obtained.

Example b 58.9 g of Z-1-(2,4-dichlorophenyl)-2-(4-chlorophenyl)-3-bromo-prop-1-ene (cf. Example a) were refluxed with 52.3 g of 3-chloroperoxybenzoic acid in 590 ml of chloroform. When the reaction was complete, the chloroform phase was washed acid-free with aqueous sodium bicarbonate solution and water, dried with sodium sulfate and evaporated down under reduced pressure. When the residue was recrystallized from methanol, two crystalline fractions were obtained:

1. 41.3 g (70.2%) of 2-bromomethyl-2-(4-chlorophenyl)-3-(2,4-dichlorophenyl)-oxirane (isomer A) of melting point 98°-99° C. and
2. 12 g (20.4%) of 2-bromomethyl-2-(4-chlorophenyl)-3-(2,4-dichlorophenyl)-oxirane (isomer B) of melting point 93°-95° C.

Preparation of the end products

Example c

A solution of 10 g of 2-bromomethyl-2-(4-chlorophenyl)-3-(2,4-dichlorophenyl)-oxirane (isomer A; cf. Example b) in 50 ml of N,N-dimethylformamide was added dropwise, at 100° C., to a melt consisting of 15.6 g of imidazole and 1.37 g of sodium methylate, the methanol liberated having been distilled off from the melt beforehand. After 8 hours, the reaction solution was poured onto water and extracted with ethyl acetate, the organic phase was washed with water, dried over sodium sulfate and evaporated down under reduced pressure, and the residue was chromatographed over a silica gel column using a 100:2 methylene chloride/methanol mixture. The purified fractions were evaporated down, and the residue was crystallized from diisopropyl ether. 4.6 g (47.5%) of 2-(1H-imidazol-1-ylmethyl)-2-(4-chlorophenyl)-3-(2,4-dichlorophenyl)-oxirane (isomer A) of melting point 102°-103° C. were obtained.

The compounds listed on pages 3 to 6 can be prepared by methods similar to those described in Examples a to c.

We claim:

1. The method of treating DNA viral infections in a patient suffering therefrom, which comprises administering to said patient an amount effective to treat said DNA viral infection of an azolylmethyloxirane of the formula I

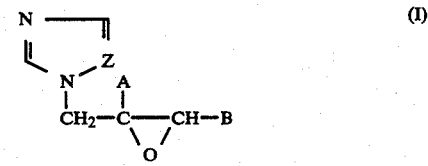

in which A and B are identical or different and independently of one another are each alkyl of 1 to 4 carbon atoms, naphthyl, biphenyl or phenyl, and the phenyl radical may be substituted by halogen, nitro, alkyl, alkoxy or haloalkyl, each of 1 to 4 carbon atoms, phenoxy or phenylsulfonyl, and Z is a CH group or nitrogen, or its physiologically tolerated salts.

2. The process of claim 1, wherein the DNA viral infection is herpes labialis, herpes genitalis, herpes Zoster, varicella, kerato-conjunctivitis herpetica, infectious mononucleosis or cytomegalovirus infections in humans; pseudorabies viral infection in pigs and cattle; rhinotracheritus virus infections in cattle; rhinopneumonitis virus infections in horses or Marek's disease in hens.

* * * * *